(12) United States Patent
Yuki et al.

(10) Patent No.: US 9,435,806 B2
(45) Date of Patent: Sep. 6, 2016

(54) IMMUNOCHROMATOGRAPHIC TEST STRIP AND MANUFACTURING METHOD THEREOF

(75) Inventors: Kumiko Yuki, Ryugasaki (JP); Yuka Sasaki, Tokyo (JP)

(73) Assignee: SEKISUI MEDICAL CO., LTD., Tokyo (JP)

(*) Notice: Subject to any disclaimer, the term of this patent is extended or adjusted under 35 U.S.C. 154(b) by 293 days.

(21) Appl. No.: 13/877,024

(22) PCT Filed: Sep. 29, 2011

(86) PCT No.: PCT/JP2011/072427
§ 371 (c)(1),
(2), (4) Date: Mar. 29, 2013

(87) PCT Pub. No.: WO2012/043746
PCT Pub. Date: Apr. 5, 2012

(65) Prior Publication Data
US 2013/0244314 A1 Sep. 19, 2013

(30) Foreign Application Priority Data
Sep. 30, 2010 (JP) .................................. 2010-222418

(51) Int. Cl.
*G01N 33/558* (2006.01)
*G01N 33/569* (2006.01)
*G01N 33/543* (2006.01)

(52) U.S. Cl.
CPC ...... *G01N 33/56983* (2013.01); *G01N 33/558* (2013.01); *G01N 33/54386* (2013.01); *G01N 2333/11* (2013.01)

(58) Field of Classification Search
None
See application file for complete search history.

(56) References Cited

U.S. PATENT DOCUMENTS 6,969,591 B2  11/2005  Hara
7,192,784 B2   3/2007  Nadaoka et al.
(Continued)

FOREIGN PATENT DOCUMENTS

EP   1 096 256 A1   5/2001
JP   2000-321277 A  11/2000
(Continued)

OTHER PUBLICATIONS

Internationa Preliminary Report on Patentability and English translation of Written Opinion, issued Apr. 18, 2013, in PCT International Application No. PCT/JP2011/072427.
(Continued)

*Primary Examiner* — Rebecca Martinez
(74) *Attorney, Agent, or Firm* — Birch, Stewart, Kolasch & Birch, LLP

(57) ABSTRACT

An immunochromatographic test strip that achieves a shorter reaction completion time and excellent sensitivity is provided. The immunochromatographic test strip comprises: (1) a conjugate pad comprising a sample-supplying section supplying a sample possibly containing an analyte and a line-shaped conjugate section containing a conjugate in which an antibody or antigen immunologically reactive with the analyte is immobilized to a label on the downstream side relative to the sample-supplying section; and (2) an insoluble membrane support having at least one detecting section to which an antibody or antigen immunologically reactive with the analyte is immobilized, the lower surface of the sample-supplying section of the conjugate pad being not in contact with the upper surface of the insoluble membrane support, the lower surface of the conjugate section of the conjugate pad being in contact with the upper surface of the insoluble membrane support.

20 Claims, 2 Drawing Sheets

(56) References Cited

U.S. PATENT DOCUMENTS

| | | | |
|---|---|---|---|
| 2003/0073147 A1* | 4/2003 | Alderete | G01N 33/558 435/7.31 |
| 2004/0161857 A1 | 8/2004 | Yugawa et al. | |
| 2004/0219690 A1 | 11/2004 | Choi et al. | |
| 2006/0046310 A1 | 3/2006 | Xia et al. | |
| 2006/0246513 A1 | 11/2006 | Bohannon | |
| 2010/0081125 A1 | 4/2010 | Xia et al. | |
| 2010/0081214 A1 | 4/2010 | Choi et al. | |
| 2012/0003756 A9 | 1/2012 | Choi et al. | |
| 2012/0107956 A1 | 5/2012 | Boehringer et al. | |

FOREIGN PATENT DOCUMENTS

| | | |
|---|---|---|
| JP | 2001-318100 A | 11/2001 |
| JP | 2005-10001 A | 1/2005 |
| JP | 2005-308485 A | 11/2005 |
| JP | 2006-194785 A | 7/2006 |
| JP | 2007-114097 A | 5/2007 |
| JP | 2009-264879 A | 11/2009 |
| JP | 2010-14507 A | 1/2010 |
| JP | 2010-14631 A | 1/2010 |
| JP | 2010-38797 A | 2/2010 |
| JP | 2010-91576 A | 4/2010 |
| JP | 2010-512537 A | 4/2010 |
| WO | WO 02/37099 A1 | 5/2002 |
| WO | WO 03/085402 A1 | 10/2003 |
| WO | WO 2004/081528 A2 | 9/2004 |
| WO | WO2008/048276 * | 4/2008 |
| WO | WO 2009/003177 A1 | 12/2008 |

OTHER PUBLICATIONS

International Search Report, dated Nov. 1, 2011, issued in PCT/JP2011/072427.

Supplementary European Search Report dated Feb. 12, 2014, issued in European Patent Application No. 11829299.

Japanese Office Action for Japanese Application No. 2012-536561, dated Sep. 9, 2015.

* cited by examiner

IMMUNOCHROMATOGRAPHIC TEST STRIP AND MANUFACTURING METHOD THEREOF

TECHNICAL FIELD

The present invention relates to an immunochromatographic test strip for detecting an analyte (a substance to be detected) such as influenza virus and a manufacturing method thereof.

BACKGROUND ART

As a method of detecting an analyte that should be detected in a sample through an antigen-antibody reaction, a measurement method using an immunochromatographic test strip has been conventionally performed. In immunochromatography, an antibody or an antigen to its antigen or antibody defined as an analyte is immobilized onto an insoluble membrane support that is a chromatograph medium to create a detecting section that is a stationary phase; a conjugate (a detection reagent), i.e., a label sensitized by an antibody or antigen capable of binding to the analyte is used as a mobile phase; the analyte is specifically reacted with the conjugate that is a mobile phase; and, in the detecting section that is a stationary phase, the analyte bound to the conjugate is specifically reacted with the antibody or antigen immobilized to the detecting section. Since metal colloid particles such as colloidal gold and colored latex particles are typically used as the label, the presence, or an amount in some cases, of the analyte in the sample is detected from color in the detecting section.

As described in Patent Literature 1, a configuration of an immunochromatographic test strip generally includes a sample pad for supplying a sample, a conjugate pad for disposing the conjugate that is the mobile phase, an insoluble membrane support developing a complex between the sample and the conjugate and having a detecting section for detection, and an absorbent pad for absorbing the sample developed through the insoluble membrane support.

However, since the conjugate is not easily released from the conjugate pad, the conventional immunochromatographic test strip configured as above has a problem that it takes time for completing the reaction or that the background tends to be high.

Although the conjugate pad is uniformly impregnated with the conjugate and dried, a step of impregnation with the conjugate makes automation of manufacturing difficult and tends to result in non-uniform impregnation with the conjugate, which may cause a problem of variation in performance.

CITATION LIST

Patent Literature

Patent Literature 1: U.S. Pat. No. 6,352,862

SUMMARY OF INVENTION

Technical Problem

An object of the present invention is to provide an immunochromatographic test strip achieving a shorter reaction completion time and excellent sensitivity. Another object of the present invention is to provide a manufacturing method that does not include a step of impregnation with a solution, that is easily automated, and that enables acquisition of immunochromatographic test strips having consistent performance.

Solution to Problem

An immunochromatographic test strip of the present invention is an immunochromatographic test strip for detecting an analyte by developing a sample possibly containing the analyte comprising (1) and (2) below:

(1) a conjugate pad, comprising a sample-supplying section for supplying a sample possibly containing the analyte, and a line-shaped conjugate section containing, on the downstream side relative to the sample-supplying section, a conjugate in which an antibody or antigen immunologically reactive with the analyte is immobilized to a label; and (2) an insoluble membrane support, comprising at least one detecting section to which an antibody or antigen immunologically reactive with the analyte is immobilized, wherein the lower surface of the sample-supplying section of the conjugate pad is not in contact with the upper surface of the insoluble membrane support, and the lower surface of the conjugate section of the conjugate pad is in contact with the upper surface of the insoluble membrane support.

The configuration of the immunochromatographic test strip above achieves excellent releasability of the conjugate from the conjugate pad, completes the reaction in a shorter time, and also achieves excellent sensitivity.

In the present invention, immobilizing an antibody or antigen means that an antigen or antibody is physically or chemically supported by a label or an insoluble membrane support.

Preferably, the conjugate section is disposed in a line shape in a direction orthogonal to the sample development direction, i.e., a line connecting the center of the sample-supplying section of the conjugate pad and the center of the upstream end of the insoluble membrane support.

The detection in the present invention includes not only qualitative detection but also quantitative detection of an analyte if it can quantitatively be determined.

In the immunochromatographic test strip, preferably, an antibody or antigen immobilized to a label and immunologically reactive with an analyte is different from an antibody or antigen immobilized to the detecting section and immunologically reactive with the analyte. Therefore, preferably, an antibody or antigen immobilized to a label and immunologically reactive with an analyte is an antibody or antigen recognizing a site of the analyte different from that recognized by an antibody or antigen immobilized to the detecting section and immunologically reactive with the analyte. Immobilization of different antibodies or antigens to the label and the detecting section leads to more excellent sensitivity.

Preferably, the center line of the line-shaped conjugate section is disposed downstream relative to the upstream end of the insoluble membrane support. Since the center line of the conjugate section is disposed downstream relative to the upstream end of the insoluble membrane support, a half or more of the lower surface of the conjugate section is in contact with the insoluble membrane support, achieving more excellent releasability of the conjugate. More preferably, the entire lower surface of the line-shaped conjugate section is in contact with the upper surface of the insoluble membrane support.

Preferably, the center line of the line-shaped conjugate section is disposed 10 to 20 mm downstream from the upstream end of the conjugate pad.

One aspect of the present invention provides a manufacturing method of the immunochromatographic test strip. The manufacturing method of the immunochromatographic test strip of the present invention comprises: applying onto a portion of a pad-shaped porous material acting as a conjugate pad, in a line shape, a conjugate solution containing a conjugate in which an antibody or antigen immunologically reactive with an analyte is immobilized to a label; drying the conjugate solution to form a conjugate section so as to create the conjugate pad having as a sample-supplying section a portion other than the conjugate section of the porous material; and stacking the conjugate pad on the upstream side of an insoluble membrane support having at least one detecting section to which an antibody or antigen immunologically reactive with the analyte is immobilized such that the lower surface of the sample-supplying section is not in contact with the insoluble membrane support while the lower surface of the conjugate section is in contact with the insoluble membrane support.

Since the manufacturing method above does not comprise a step of impregnating the porous material with a conjugate, and a conjugate section is formed by application of a solution, which is easily automated, the manufacturing can entirely be automated and, since an application amount of the solution can relatively easily controlled, the performance of the acquired immunochromatographic test strip is easily maintained consistently.

Advantageous Effects of Invention

The immunochromatographic test strip of the preset invention can be made up of a conjugate pad and an insoluble membrane support since a conjugate section is formed in a line shape and the conjugate section and the insoluble membrane support are in a certain positional relationship. Moreover, the immunochromatographic test strip achieves excellent releasability of the conjugate from the conjugate pad, completes a reaction in a shorter time, and also achieves excellent sensitivity.

Furthermore, the releasability and the sensitivity are made more excellent when the center line of the line-shaped conjugate section is disposed downstream relative to the upstream end of the insoluble membrane support.

Since the manufacturing method of the present invention does not include a step of impregnating an entire pad with a conjugate solution as in the case of conventional conjugate pads, the manufacturing of the conjugate pad is easily automated. Since the conjugate pad is manufactured by applying the conjugate in a line shape, the amount and application position of the conjugate are easily adjusted and made uniform and, as a result, the immunochromatographic test strips having consistent performance are acquired.

DESCRIPTION OF EMBODIMENTS (Analyte)

Figure 1:
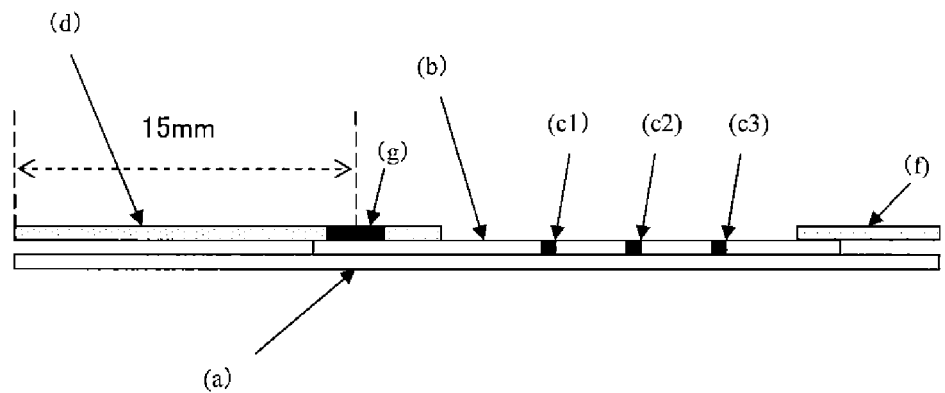
FIG. 1 is a diagram of an immunochromatographic test strip of the present invention (Device Production Examples 2, 3, and 4).

In the preset invention, analytes include viruses and physiologically active substances that can generally be measured by utilizing antigen-antibody reaction, such as proteins.

The viruses include, for example, influenza viruses such as influenza A virus and influenza B virus, hepatitis B virus, hepatitis C virus, and human immunodeficiency virus, and the proteins include, for example, human hemoglobin, hepatitis B antibody, hepatitis C antibody, and human immunodeficiency virus antibody. In particular, preferably, influenza virus is employed as an analyte and, more preferably, a plurality of detecting sections described later are formed to detect influenza A virus and influenza B virus as analytes.

(Sample)

In the present invention, samples possibly containing an analyte include substances mainly derived from a living body (organism), such as body fluid, and extracts acquired by extracting analytes therefrom. The substances derived from a living body (organism) specifically include blood; urine; feces; nasal secretion and nasal secretion aspirate derived from a nostril, a nasal cavity, a pharynx, and a nasopharynx; secretion collected as sputum or a swab specimen; and saliva. In particular, if the analyte is influenza virus, preferably, the samples are nasal secretion and nasal secretion aspirate derived from a nostril, a nasal cavity, a pharynx, and a nasopharynx, and secretion collected as sputum or a swab specimen. The substances derived from a living body (organism) and the extract thereof may be directly used as a sample or may be diluted by a diluent as needed before used as a sample. The substances and the extract thereof may be filtered as needed before used as a sample.

(Antibody or Antigen Immunologically Reactive with Analyte)

An antibody or antigen immunologically reactive with an analyte used in the present invention is an antibody or antigen capable of binding to the analyte, and an antibody is preferable when the analyte is a virus or an antigen while an antigen is preferable when the analyte is an antibody. The antibody or antigen immunologically reactive with an analyte is immobilized to a label and a detecting section described later. Although the antibody or antigen immobilized to the label may be the same as that immobilized to the detecting section, preferably, different antibodies or antigens are immobilized to the label and the detecting section. By using different antibodies or antigens for an antibody or antigen immobilized to the label and an antibody or antigen immobilized to the detecting section, the acquired immunochromatographic test strip can suppress competition between the reaction of an analyte bound to the conjugate with an antibody or antigen of the detecting section and the reaction of an analyte bound to the conjugate with an unreacted conjugate, and can increase reactivity between the analyte bound to the conjugate and the antibody or antigen of the detecting section, resulting in favorable sensitivity of the immunochromatographic test strip. The term "different" in this context mean that varieties are different from each other, and refer to antibodies recognizing different epitopes in the case of antibodies and refer to antigens having different epitopes in the case of antigens.

Preferably, antibodies immobilized to the label and the detecting section are monoclonal antibodies. Using a monoclonal antibody can increase specificity of reaction.

If the analyte is influenza virus, antibodies immobilized to the label and the detecting section may be any antibody capable of detecting influenza virus and, preferably, the antibody is an anti-influenza virus monoclonal antibody such as an anti-influenza A virus monoclonal antibody and an anti-influenza B virus monoclonal antibody.

In addition to whole molecules of these antibodies, functional fragments of antibodies having antigen-antibody reaction activity are also considered as antibodies in the present invention. Functional fragments of antibodies include those acquired through an immunological operation to an animal as well as those acquired by using a gene-recombination technique, and chimeric antibodies. Functional fragments of antibodies include, for example, F(ab')$_2$ and Fab'. These functional fragments can be produced by treating the antibodies with proteolytic enzymes (e.g., pepsine and papain). In particular, preferably, F(ab')$_2$ is used as an antibody immobilized to the label in the present invention. By using F(ab')$_2$ that is a functional antibody fragment on the label, for example, the size of a conjugate formed by binding an antibody to the label can be reduced, resulting in excellent developability in a conjugate pad and an insoluble membrane support. For some analytes, specificity of reaction can be increased by using a functional antibody fragment.

(Label)

A label used in the present invention can be a known label conventionally used for an immunochromatographic test strip. For example, the labels are preferably metal colloid particles such as colloidal gold particles and colloidal platinum particles, colored latex particles, and magnetic particles, particularly preferably the colloidal gold particles.

With regard to the particle diameter of the label, preferably, a label with a suitable particle diameter are used depending on the label to be used. For example, if colloidal gold particles are used for the label, the particle diameter is preferably 20 to 60 nm, particularly preferably 45 to 55 nm. The colloidal gold particles can be manufactured with a commonly known method, for example, by dripping and stirring a heated tetrachloroauric(III) acid solution into a trisodium citrate solution.

(Conjugate)

A conjugate used in the present invention is the label as described above to which an antibody or antigen immunologically reactive with an analyte is immobilized. If the analyte is influenza virus, preferably, the conjugate is colloidal gold particles with an anti-influenza virus monoclonal antibody immobilized.

A method of immobilizing an antibody or antigen immunologically reactive with an analyte to a label may be physisorption, chemical bond, etc., and physisorption is generally used for the immobilization. For example, if an anti-influenza virus monoclonal antibody is immobilized to colloidal gold particles, the colloidal gold particles and the anti-influenza virus monoclonal antibody are usually added to a buffer solution and immobilized by physisorption. In this case, antibody concentration is preferably adjusted to 20 to 100 µg/mL. Preferably, the buffer solution and pH thereof are, for example, a 0.5 to 5 mM phosphate buffer solution (pH 6 to 7) or a 0.5 to 5 mM boric-acid buffer solution (pH 8 to 9.5).

On the label such as colloidal gold particles, the region bound to neither an antibody nor antigen is preferably blocked with BSA etc.

(Conjugate Pad)

A conjugate pad used in the present invention is made of a pad-shaped porous material capable of developing a sample and retaining a conjugate and has a sample-supplying section and a line-shaped conjugate section as portions thereof. A porous material portion containing no conjugate is present between the sample-supplying section and the conjugate section and a sample supplied to the sample-supplying section is preferably developed through the porous material and reaches the conjugate section.

The sample-supplying section is a site for supplying a sample possibly containing an analyte, is formed in a portion of the porous material, and is located on the upstream side of the conjugate pad.

The conjugate section is a site containing a conjugate and is formed into a line shape on the porous material on the downstream side relative to the sample-supplying section. The line-shaped conjugate section is preferably disposed in a line shape in a direction orthogonal to a sample development direction, i.e., a line connecting the center of the sample-supplying section of the conjugate pad and the center of the upstream end of the insoluble membrane support described later. The line-shaped conjugate section is desirably disposed downstream relative to the center of the length in the sample development direction of the conjugate pad. Considering a typical size of an immunochromatographic test strip, the center line of the line-shaped conjugate section is disposed preferably 10 to 20 mm downstream and more preferably 12 to 18 mm downstream from the upstream end of the conjugate pad.

A porous material portion containing no conjugate may exist on the downstream side from the conjugate section of the conjugate pad and it does not form the conjugate section.

A line width of the line-shaped conjugate section may be such a width that an amount of conjugate necessary for detecting an analyte can be contained, and is desirably 3 to 5 mm.

The conjugate pad is stacked on an insoluble membrane support described later such that the lower surface of the downstream end portion of the conjugate pad is in contact with the upper surface of the insoluble membrane support. The conjugate pad is stacked on the insoluble membrane support such that the lower surface of the sample-supplying section is not in contact with the upper surface of the insoluble membrane support while the lower surface of the conjugate section is in contact with the upper surface of the insoluble membrane support. The stacking merely requires contact between the lower surface of the conjugate pad and the upper surface of the insoluble membrane support and it is not necessary to fix the surfaces. A portion of the lower surface of the conjugate section may contact with the upper surface of the insoluble membrane support, and preferably, the contacting portion is a half or more of the lower surface of the conjugate section. It is also desirable that the entire lower surface of the conjugate section is in contact with the upper surface of the insoluble membrane support. In other words, the contact of a "half or more of the lower surface" in this context means that the center line of the line-shaped conjugate section is disposed downstream relative to the upstream end of the insoluble membrane support. If no contact is made between the lower surface of the conjugate section and the upper surface of the insoluble membrane support, the releasability of conjugates from the conjugate section and the developability of conjugates deteriorate and the background increases, reducing the visibility of the detecting section.

The sample-supplying section is formed upstream relative to the conjugate section of the conjugate pad and this portion corresponds to a portion acting as a so-called sample pad disposed on a conventional immunochromatographic test strip. When a sample possibly containing an analyte is supplied to the sample-supplying section of the conjugate pad, the sample flows from the sample-supplying section on the upstream side through the porous material portion containing no conjugate to the conjugate section on the downstream side. In the conjugate section, the analyte (influenza virus) in the sample and the conjugate (colloidal gold particles with the anti-influenza virus monoclonal antibody immobilized) form a complex (aggregate). The sample is then developed into the insoluble membrane support disposed in contact with the lower surface of the conjugate section.

The porous material making up the conjugate pad may be a pad made of nonwoven fibers of paper, a cellulose mixture, nitrocellulose, polyester, acrylonitrile copolymer, glass, rayon, etc. In particular, a pad made of glass fibers (glass fiber pad) is preferable.

(Insoluble Membrane Support)

The insoluble membrane support used in the present invention has at least one detecting section to which an antibody or antigen immunologically reactive with an analyte is immobilized. The antibody or antigen immunologically reactive with an analyte can be immobilized to the insoluble membrane support with a conventionally known method. In the case of a lateral flow immunochromatographic test strip, the immobilization is performed as follows. After a solution containing a predetermined concentration of the antibody or antigen is prepared, the solution is applied in a line shape to the insoluble membrane support by using an apparatus having a mechanism capable of moving a nozzle horizontally while discharging the solution at a constant rate from the nozzle, and is dried for immobilization.

The concentration of the antibody or antigen in the solution is preferably 0.1 to 5 mg/mL, more preferably 0.5 to 2 mg/mL. In the case of a lateral flow immunochromatographic test strip, the amount of the antibody or antigen immobilized to the insoluble membrane support can be optimized by adjusting the discharge rate from the nozzle of the apparatus and a preferred rate is 0.5 to 2 µL/cm.

An assay using the lateral flow immunochromatographic test strip above is a measurement method in which the sample supplied from a portion of the conjugate pad in contact with the insoluble carrier is developed such that the sample moves in a direction parallel to the insoluble membrane support due to capillarity.

The solution containing a predetermined concentration of the antibody or antigen can be prepared by adding the antibody or antigen to a buffer solution. A type of the buffer solution may be a typically used buffer solution such as a phosphate buffer solution, a Tris buffer solution, and a Good's buffer solution. The solution may preferably have pH in a range of 6.0 to 9.5, more preferably 6.5 to 8.5, further preferably 7.0 to 8.0. The buffer solution may further contain salts such as sodium chloride, stabilizer and preservative such as sucrose, and antiseptic such as ProClin. The salts includes those contained for adjustment of ionic strength, such as sodium chloride, as well as those added for the purpose of adjustment of pH of the buffer solution, such as sodium hydroxide.

After the antibody or antigen is immobilized to the insoluble membrane support, a portion other than the site of immobilization of the antibody or antigen can be blocked by using a typically used blocking agent in a form of solution or vapor.

A control capture reagent conventionally used for an immunochromatographic test strip may be immobilized to the insoluble membrane support. The control capture reagent is a reagent for ensuring reliability of the assay and captures a control reagent contained in the conjugate pad. For example, if labeled KLH is contained as a control reagent in the conjugate pad, an anti-KLH antibody may be the control capture reagent. The position of immobilization of the control capture reagent can appropriately be selected in accordance with design of the assay system.

A membrane making up the insoluble membrane support used in the present invention can be a known membrane conventionally used as an insoluble membrane support of an immunochromatographic test strip. For example, the membrane may be one of those made of fibers of polyethylene, polyethylene terephthalate, nylons, glass, polysaccharide such as cellulose and cellulose derivatives, ceramics, etc. Specifically, the membrane may be glass fiber filter paper, cellulose filter paper, etc., commercially available from Sartorius AG, Millipore Corporation, Toyo Roshi Kaisha, Ltd., Whatman, Inc., etc. In particular, UniSart (registered trademark) CN140 from Sartorius is preferable. By selecting a pore diameter and a structure of the insoluble membrane support as needed, the flow rate in the insoluble membrane support of the complex of the conjugate and the analyte in the sample can be controlled.

(Absorbent Pad)

In the immunochromatographic test strip of the present invention, preferably, an absorbent pad is disposed on the downstream end portion of the insoluble membrane support. The absorbent pad is a site having liquid absorbability controlling the development of the sample through absorption of the sample moving in and passing through the insoluble membrane support. The absorbent pad can be a known absorbent pad conventionally used for an immunochromatographic test strip and, for example, a sheet of filter paper can be used. Preferably, 740-E from Whatman is used.

(Immunochromatographic Test Strip)

The immunochromatographic test strip of the present invention includes the conjugate pad and the insoluble membrane support. The conjugate pad and the insoluble membrane support are stacked such that the lower surface of the conjugate pad is in contact with the upper surface of the insoluble membrane support. The conjugate pad is disposed such that the lower surface of the sample-supplying section of the conjugate pad is not in contact with the upper surface of the insoluble membrane support and that a portion or whole, preferably a half or more, of the lower surface of the conjugate section of the conjugate pad is in contact with the upper surface of the insoluble membrane support. As described above, preferably, the absorbent pad is additionally disposed on the downstream end portion of the insoluble membrane support.

The immunochromatographic test strip is preferably disposed on a solid phase support such as a plastic adhesive sheet. The solid phase support is made of a material not hindering the capillary flow of the sample and the conjugate. The immunochromatographic test strip may be fixed to the solid phase support with an adhesive etc. In this case, an adhesive component etc., are also made of a material not hindering the capillary flow of the sample and the conjugate. A polyester film etc., can be used for lamination in order to increase the mechanical strength of the insoluble membrane support and to prevent evaporation of water (drying) during the assay. The immunochromatographic test strip can be used after stored in or mounted on an appropriate container (housing) with consideration given to the size of the immunochromatographic test strip, the manner and position of addition of the sample, the position of formation of the detecting section of the insoluble membrane support, the signal detection method, etc., and such a stored/mounted state is referred to as a "device".

The immunochromatographic test strip of the present invention includes a conjugate pad and an insoluble membrane support and may include another reagent or constituent element depending on the measurement condition and the sample. Another reagent may be a blocking reagent preventing non-specific reactions, for example, and another constituent element may be a 3rd pad for removing a component in a sample unnecessary for measurement.

(Manufacturing Method of Immunochromatographic Test Strip)

Although the manufacturing method of the immunochromatographic test strip is not particularly limited, preferably, a conjugate solution is applied in a line shape to a portion of a pad-shaped porous material (a portion to be the conjugate section) and dried to create a conjugate pad and this conjugate pad is then brought into contact with an insoluble membrane support having a detecting section to form the immunochromatographic test strip.

For example, the manufacturing method of the immunochromatographic test strip of the present invention has the following steps (1) to (3):

(1) a step of applying a conjugate solution containing a conjugate in which an antibody or antigen immunologically reactive with an analyte is immobilized to a label in a line shape onto a portion of a pad-shaped porous material acting as a conjugate pad and drying the conjugate solution to form a conjugate section so as to create the conjugate pad having a portion other than the conjugate section as a sample-supplying section;

(2) a step of preparing an insoluble membrane support having at least one detecting section to which an antibody or antigen immunologically reactive with the analyte is immobilized; and (3) a step of stacking the conjugate pad acquired at (1) on the upstream side of the insoluble membrane support prepared at (2) such that the lower surface of the sample-supplying section is not in contact with the insoluble membrane support while the lower surface of the conjugate section is in contact with the insoluble membrane support.

The conjugate solution is a typically used buffer solution further containing a conjugate and the concentration of the conjugate is appropriately adjusted depending on the amount of conjugate to be contained in the conjugate section.

The conjugate solution is applied to a portion of a pad-shaped porous material acting as the conjugate pad (a portion to be the conjugate section) by using a nozzle etc., capable of discharging the solution at a constant rate. The application makes the control of application amount easier as compared to impregnation etc., and the application of conjugate solution makes the control of conjugate amount easier, resulting in excellent consistency in the amount of conjugate on the acquired conjugate pad. Subsequently, the conjugate pad is acquired after drying by heating, natural drying, etc.

The conjugate pad has a sample-supplying section, and the sample-supplying section is a porous material portion containing no conjugate and can be disposed at a suitable position depending on the developability of the sample, a container storing the immunochromatographic test strip, etc.

The method of forming the insoluble membrane support and the method of stacking the conjugate pad and the insoluble membrane support are as described above.

(Others)

The production of the immunochromatographic test strip of the present invention can be implemented by modifying and altering the method described in Examples as needed.

A method of measuring a signal derived from a conjugate may be implemented in accordance with a known method and, for example, the absorbance or the intensity of reflected light may be measured.

EXAMPLES

Although the present invention will then specifically be described with examples, the scope of the present invention is not limited to the examples.

[Preparation of Anti-Influenza Virus Monoclonal Antibody]

Anti-influenza A virus monoclonal antibodies (Clone#622212, Clone#62241A) and anti-influenza B virus monoclonal antibodies (Clone#612108, Clone#614216) used in the following tests were acquired by using recombinant influenza nucleoprotein as an antigen to immunize mice with a method typically used for producing a monoclonal antibody by those skilled in the art.

Device Production Example 1

Production of Conventional Immunochromatographic Test Strip (3-Pad Type)

1) Production of Anti-Influenza Virus Monoclonal Antibody Labeled by Colloidal Gold Particles (Conjugate)

An anti-influenza A virus monoclonal antibody and an anti-influenza B virus monoclonal antibody were prepared with the following antibody concentrations and buffer solution conditions. One (1) mL of each of the antibody solutions was added to 20 mL of a 1 OD/mL colloidal gold particles solution (having a particle diameter of 50 nm) and stirred at room temperature for 10 minutes. After adding 2 mL of a 10% bovine serum albumin (BSA) aqueous solution, the colloidal gold particles-anti-influenza A virus monoclonal antibody-mixture and the colloidal gold-anti-influenza B virus monoclonal antibody-mixture were further stirred for 5 minutes and centrifuged at 10,000 rpm at 10° C. for 45 minutes to obtain sediments (conjugates). To the acquired conjugates, 1.2 mL of Conjugate Dilution Buffer (manufactured by Scripps) was added to suspend the conjugates. The absorbance of each of the conjugates was measured at 531 nm (the maximum absorption wavelength of the colloidal gold particles used). The measurement of the absorption was performed in the same way in the subsequent tests.

i) Mouse anti-influenza A virus monoclonal antibody
Clone#622212 (25 µg/mL), 2 mM phosphate buffer solution ii) Mouse anti-influenza B virus monoclonal antibody
Clone#612108 (35 µg/mL), 2 mM phosphate buffer solution 2) Production of Conjugate Pad The conjugates prepared at 1) were mixed with 1.33% casein, 4% sucrose solution (pH 7.5) at 8 to 20 OD/mL to produce a conjugate solution, and a glass fiber pad having a certain volume (No. 8964, Pall Corporation) was impregnated with 1.2 volumes of the conjugate solution relative to the volume of the pad. The pad was heated and dried at 70° C. for 30 minutes in a dry oven to form a conjugate pad. If an additive such as a sensitizer was added, a necessary amount was added to the detection reagent before performing the same operation.

3) Production of Insoluble Membrane Support to which Anti-Influenza Virus Monoclonal Antibody is Immobilized (Antibody-Immobilized Membrane)

Twenty (20) mM TBS (pH 8.0) containing the following anti-influenza A virus monoclonal antibody prepared at 2.0 mg/mL and 2.5% sucrose was applied in a line shape to a nitrocellulose membrane (UniSart CN140, Sartorius) at one end of the shorter sides by using an immunochromatography dispenser "XYZ3050" (BIO DOT) set to 1.0 µL/cm. Similarly, 20 mM TBS (pH 8.0) containing the following anti-influenza B virus monoclonal antibody prepared at 1.0 mg/mL and 2.5% sucrose was applied in a line shape by using the immunochromatography dispenser set to 1.0 µL/cm. For a control antibody, 10 mM TBS (pH 8.0) containing a goat anti-mouse IgG prepared at 0.75 mg/mL and 2.5% sucrose was applied in a line shape by using the immunochromatography dispenser set to 1.0 µL/cm. The lines were applied in the order of the anti-influenza A virus monoclonal antibody (c1), the anti-influenza B virus monoclonal antibody (c2), and the control antibody (c3) from the upstream side of the assembled test strip.

The membrane was dried at 70° C. for 45 minutes in a dry oven to obtain an antibody-immobilized membrane. The goat anti-mouse IgG specifically recognizes an $F(ab')_2$ portion of an antibody.

i) Mouse anti-influenza A virus monoclonal antibody (antibody recognizing an epitope different from the antibody used for the conjugate)

Clone#62241A ii) Mouse anti-influenza B virus monoclonal antibody (same as above)

Clone#614216

(iii) Goat anti-mouse IgG

4) Production of Sample Pad

A glass fiber pad (Lydall) was used as a sample pad.

5) Production of Immunochromatographic Test Strip

Figure 4:
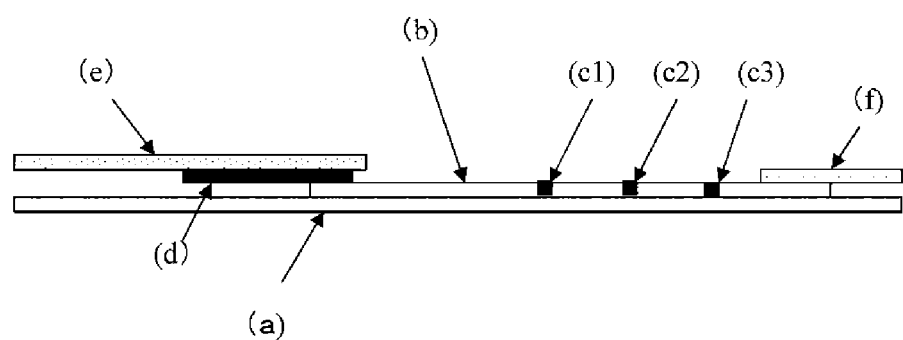
FIG. 4 is a diagram of a conventional immunochromatographic test strip (Device Production Example 1).

To a plastic adhesive sheet (a), the antibody-immobilized membrane (b) was affixed; the conjugate pad (d) produced in 2) was then placed and disposed; the sample pad (e) was also placed and disposed to overlap the conjugate pad; and the absorbent pad (f) (740-E, Whatman, Inc.) was placed and disposed at the end of the other side. The structure formed by overlapping the constituting elements as described above was cut to a certain width to produce the immunochromatographic test strip. At the time of assay, the immunochromatographic test strip was stored in or mounted on a dedicated plastic housing (having a sample supply window and a detection window not depicted in FIG. 4) into a form of an immunochromatographic test device. FIG. 4 is a schematic of a configuration of a conventional immunochromatographic test strip.

Device Production Example 2

Production of Immunochromatographic Test Strip of the Present Invention (2-Pad Type)

1) Production of Anti-Influenza Virus Monoclonal Antibody Labeled by Colloidal Gold Particles (Conjugate)

The antibodies were produced in the same way as 1 above.

2) Production of Conjugate Pad

The conjugates prepared at 1) were mixed with 1.33% casein, 4% sucrose solution (pH 7.5) at 8 to 20 OD/mL to produce a conjugate solution, and a glass fiber pad having a certain volume (No. 8964, Pall Corporation) was impregnated with the conjugate solution such that a line with the width of 5 mm is formed at a position of 15 mm from the upstream end of the pad. The pad was heated and dried at 70° C. for 30 minutes in a dry oven to form a conjugate pad. If an additive such as a sensitizer was added, a necessary amount was added to the detection reagent before performing the same operation. Although the conjugate pad and the sample pad are separated in the conventional immunochromatographic test strip described in 1 above, the immunochromatographic test strip of the present invention has no sample pad and has the sample-supplying section (not depicted in FIG. 2) and the line-shaped conjugate section (g) present in a portion of the conjugate pad.

3) Production of Anti-Influenza Virus Monoclonal Antibody-Immobilized Membrane

The membrane was produced in the same way as 1 above.

4) Production of Immunochromatographic Test Strip

The line-shaped conjugate section (g) formed at a position of 15 mm from the upstream end of the conjugate pad is formed such that the upstream end thereof is located downstream relative to the upstream end of the antibody-immobilized membrane (b), and is formed at a position away from the downstream end. Therefore, the conjugate section (g) has the lower surface entirely in contact with the upper surface of the antibody-immobilized membrane. The immunochromatographic test strip was formed into an immunochromatographic test device as was the case with the Device Production Example 1. FIG. 1 is a schematic of a configuration of the immunochromatographic test strip of the present invention.

Device Production Example 3

Production of Immunochromatographic Test Strip of the Present Invention

The test strip was produced in the same way as the Device Production Example 2 except that the antibodies used was changed from whole antibodies (i.e., non-fragmented antibodies) to fragments thereof, i.e., $F(ab')_2$.

Device Production Example 4

Production of Immunochromatographic Test Strip of the Present Invention

The center line of the line-shaped conjugate section (g) formed at a position of 15 mm from the upstream end of the conjugate pad is disposed downstream relative to the upstream end of the antibody-immobilized membrane (b) while the upstream end of the conjugate section (g) is disposed upstream relative to the upstream end of the antibody-immobilized membrane (b). Therefore, although a half or more of the lower surface of the conjugate section (g) is in contact with the upper surface of the antibody-immobilized membrane, the conjugate section (g) has a portion not in contact with the antibody-immobilized membrane. The immunochromatographic test strip was formed into an immunochromatographic test device as was the case with the Device Production Example 1.

Device Production Example 5 (Reference Example)

Production of Immunochromatographic Test Strip

Figure 3:
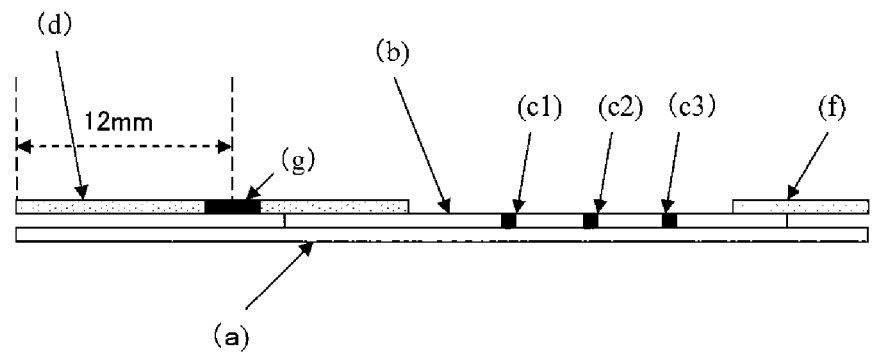
FIG. 3 is a diagram of an immunochromatographic test strip of a reference example (Device Production Example 5).

The conjugate section is formed at a position of 12 mm from the upstream end of the conjugate pad with the downstream end of the conjugate section located upstream relative to the upstream end of the antibody-immobilized membrane. Therefore, the lower surface of the conjugate section is not in contact with the antibody-immobilized membrane. The immunochromatographic test strip was formed into an immunochromatographic test device as was the case with the Device Production Example 1. FIG. 3 is a schematic of a configuration of the immunochromatographic test strip of this Reference Example.

Device Production Example 6

Production of Immunochromatographic Test Strip of the Present Invention

The conjugate section is formed at a position of 12 mm from the upstream end of the conjugate pad with the center line disposed upstream relative to the upstream end surface of the antibody-immobilized membrane while the downstream end of the conjugate section is disposed downstream relative to the upstream end of the antibody-immobilized membrane. Therefore, less than half of the lower surface of the conjugate section is in contact with the antibody-immobilized membrane. The immunochromatographic test strip was formed into an immunochromatographic test device as was the case with the Device Production Example 1.

Device Production Example 7

Production of Immunochromatographic Test Strip of the Present Invention

Figure 2:
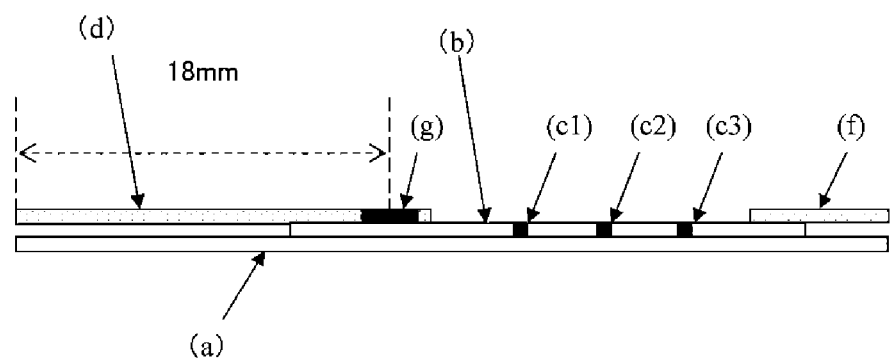
FIG. 2 is a diagram of an immunochromatographic test strip of the present invention (Device Production Example 7).

The test strip was produced in the same way as the Device Production Example 3 except that the conjugate section was formed at the most downstream end portion of the conjugate pad, i.e., at a position of 18 mm from the conjugate pad upstream end. FIG. 2 is a schematic of a configuration of the immunochromatographic test strip of the present invention.

Example 1

The immunochromatographic test devices produced in the Device Production Examples 1 to 7 were used for performing an influenza virus-detection test.

1. Test Method (1) Sample

The following antigens were diluted with PBS (pH 7.4) containing 2% BSA to 1/160 to 1/2560 to acquire simulation samples.

Influenza virus A antigen: derived from Kitakyusyu 159/93 strain

Influenza virus B antigen: derived from Lee 40 strain (2) Procedure

Through the sample supply window of the immunochromatographic test device, 115 μL of the simulation sample adjusted at (1) was added and, after 15 minutes, the presence of a red detection spot on the antibody-immobilized membrane was observed through a detection window.

(3) Evaluation Criteria (3-1) Detection Sensitivity

Judgment was made based on the following three levels:

+ positive;
− negative; and
+/− judgment suspended (level at which judgment can barely be made).

TABLE 1

Specifications of devices

| | Device Production Example | | | | | | |
|---|---|---|---|---|---|---|---|
| | 1 | 2 | 3 | 4 | 5 | 6 | 7 |
| | Conventional art | Present invention | Present invention | Present invention | Reference example | Present invention | Present invention |
| Figure | FIG. 4 | FIG. 1 | FIG. 1 | Not shown | FIG. 3 | Not shown | FIG. 2 |
| Structure | 3 pad | 2pad | 2pad | 2pad | 2pad | 2pad | 2pad |
| Antibody | Whole | Whole | F (ab') 2 | F (ab') 2 | F (ab') 2 | F (ab') 2 | F (ab') 2 |
| Conjugate width (mm) | (Whole) | 5 | 5 | 10 | 5 | 10 | 5 |
| Distance between upstream end of conjugate pad and center line of conjugate line (mm) | — | 15 | 15 | 15 | 12 | 12 | 18 |
| Relative position of center line of conjugate line to upstream end of membrane (mm) | — | Inside | Inside | Inside | Outside | Outside | Inside |
| Presence of portion within conjugate section contacting with membrane | — | Yes | Yes | Yes | No | Yes | Yes |
| Location of conjugate section | (Whole) | Downstream end portion (not most downstream end portion) | Downstream end portion (not most downstream end portion) | Downstream end portion (not most downstream end portion) | Downstream end portion (not most downstream end portion) | Downstream end portion (not most downstream end portion) | Most downstream end portion |

(3-2) Background Intensity

Judgment was made based on the following three levels:
- ++ background intensity is so high that visibility is reduced;
- + background intensity is high although judgment is not affected; and
- − background has no effect.

2. Test Results

The results are described in Table 2.

(1) Difference Between 3-Pad and 2-Pad

Comparing the results of the Device Production Examples 1 and 2, it was confirmed that the 2-pad type of the present invention can detect both the A-antigen and the B-antigen at lower concentration and has higher detection sensitivity. The 2-pad type of the present invention had lower background intensity and excellent visibility.

(2) Difference Between Whole Antibody and F(Ab')$_2$ Antibody

Comparing the results of the Device Production Examples 2 and 3, it was confirmed that the Device Production Example 3 using the fragments of the antibodies enables detection of both the A-antigen and the B-antigen at lower concentration and achieves higher detection sensitivity.

(3) With Regard to the Position of Conjugate Line of Conjugate Pad and Overlap with Insoluble Membrane Support Comparison of the Device Production Examples 3 to 7 reveals the following matters.

(i) When a conjugate section is formed in a line shape on a portion of the conjugate pad without impregnating the whole pad with a conjugate as in the conventional case, sufficient detection sensitivity was acquired and, when the position of the line was located at a position of 12 to 18 mm from the upstream end of the conjugate pad, favorable sensitivity was acquired.

(ii) With regard to positional relationship between the conjugate section and the insoluble membrane support, a portion of the conjugate section must have the lower surface in contact with the upper surface of the insoluble membrane support, and the center line of the conjugate section is desirably disposed downstream (inside) relative to the upstream end of the insoluble membrane support. Therefore, it is desirable that a half or more of the lower surface of the conjugate section is in contact with the insoluble membrane support.

TABLE 2

| | | | Device production example | | | | | | | | | | | | | |
|---|---|---|---|---|---|---|---|---|---|---|---|---|---|---|---|---|
| | | | 1 | | 2 | | 3 | | 4 | | 5 | | 9 | | 7 | |
| | | | Structure | | | | | | | | | | | | | |
| | | | 3Pad | | 2Pad | | | | | | | | | | | |
| | | | Antibody | | | | | | | | | | | | | |
| | | | Whole | | Whole | | F(ab')2 | | | | | | | | | |
| | | | Location of conjugate * | | | | | | | | | | | | | |
| | | | — | | 15 mm | | 15 mm | | 15 mm | | 12 mm | | 12 mm | | 18 mm | |
| Antigen | Dilution fold | | A | B | A | B | A | B | A | B | A | B | A | B | A | B |
| A/Kitakyusyu | 1/320 | n = 1 | + | − | + | − | + | − | + | − | + | − | + | − | + | − |
| | | n = 2 | + | − | + | − | + | − | + | − | + | − | + | − | + | − |
| | 1/640 | n = 1 | + | − | + | − | + | − | + | − | + | − | + | − | + | − |
| | | n = 2 | + | − | + | − | + | − | + | − | + | − | + | − | + | − |
| | 1/1280 | n = 1 | + | − | + | − | + | − | + | − | + | − | + | − | + | − |
| | | n = 2 | + | − | + | − | + | − | + | − | + | − | + | − | + | − |
| | 1/2560 | n = 1 | − | − | +/− | − | + | − | + | − | + | − | + | − | +/− | − |
| | | n = 2 | − | − | +/− | − | + | − | + | − | + | − | + | − | − | − |
| | 1/5120 | n = 1 | − | − | − | − | − | − | − | − | − | − | − | − | − | − |
| | | n = 2 | − | − | − | − | − | − | − | − | − | − | − | − | − | − |
| B/Lee | 1/160 | n = 1 | − | + | − | + | − | + | − | + | − | + | − | + | − | + |
| | | n = 2 | − | + | − | + | − | + | − | + | − | + | − | + | − | + |
| | 1/320 | n = 1 | − | + | − | + | − | + | − | + | − | + | − | + | − | + |
| | | n = 2 | − | + | − | + | − | + | − | + | − | + | − | + | − | + |
| | 1/640 | n = 1 | − | + | − | + | − | + | − | + | − | + | − | + | − | + |
| | | n = 2 | − | + | − | + | − | + | − | + | − | + | − | + | − | + |
| | 1/1280 | n = 1 | − | − | − | +/− | − | + | − | + | − | + | − | + | − | +/− |
| | | n = 2 | − | − | − | +/− | − | + | − | + | − | + | − | + | − | +/− |
| | 1/2560 | n = 1 | − | − | − | − | − | − | − | − | − | − | − | − | − | − |
| | | n = 2 | − | − | − | − | − | − | − | − | − | − | − | − | − | − |
| Background intensity | | | ++ | | − | | − | | + | | ++ | | + | | − | |
| | | | Low visibility | | | | | | No difficulty in determination | | Low visibility | | No difficulty in determination | | | |

A: Mouse anti-influenza A virus antibody, B: Mouse anti-influenza B virus antibody
* Distance between upstream end of conjugate pad and center line of conjugate line (mm)

INDUSTRIAL AVAILABILITY

According to the immunochromatographic test strip of the present invention, immunochromatographic test strips that achieve a shorter reaction-completion time and excellent sensitivity can be provided. If the manufacturing method of the immunochromatographic test strip of the present invention is used, the manufacturing method does not include the step of impregnation with a conjugate solution and is easily automated, and immunochromatographic test strips having consistent performance can be acquired.

REFERENCE SIGNS LIST (a) plastic adhesive sheet
(b) antibody-immobilized membrane
(c1) anti-influenza A virus monoclonal antibody
(c2) anti-influenza B virus monoclonal antibody
(c3) control antibody
(d) conjugate pad
(e) sample pad
(f) absorbent pad
(g) conjugate section

The invention claimed is:

1. An immunochromatographic test strip for detecting an analyte by developing a sample possibly containing the analyte comprising:
   (1) a conjugate pad, comprising a sample-supplying section for supplying a sample possibly containing the analyte, and a line-shaped conjugate section with a line width of 3-5 mm containing, on the downstream side exclusive to the edge of the conjugate pad relative to the sample-supplying section, a conjugate in which an antibody or antigen immunologically reactive with the analyte is immobilized to a label; and
   (2) an insoluble membrane support, comprising at least one detecting section to which an antibody or antigen immunologically reactive with the analyte is immobilized,
   wherein the lower surface of the sample-supplying section of the conjugate pad is not in contact with the upper surface of the insoluble membrane support, and the lower surface of the conjugate section of the conjugate pad is in contact with the upper surface of the insoluble membrane support.

2. The immunochromatographic test strip according to claim 1, wherein the antibody or antigen immunologically reactive with the analyte and immobilized to the label is different from the antibody or antigen immunologically reactive with the analyte and immobilized to the detecting section.

3. The immunochromatographic test strip according to claim 1 or 2, wherein a center line of the line-shaped conjugate section is disposed downstream relative to an upstream end of the insoluble membrane support.

4. The immunochromatographic test strip according to claim 1, wherein the entire lower surface of the line-shaped conjugate section is in contact with the upper surface of the insoluble membrane support.

5. The immunochromatographic test strip according to claim 1, wherein the test strip is in a lateral flow format.

6. The immunochromatographic test strip according to claim 1, wherein the analyte is influenza virus, and wherein the antibody or antigen immunologically reactive with the analyte and immobilized to the label and the antibody or antigen immunologically reactive with the analyte and immobilized to the detecting section are anti-influenza virus monoclonal antibodies.

7. The immunochromatographic test strip according to claim 6, wherein the anti-influenza virus monoclonal antibody immobilized to the label is an $F(ab')_2$ fragment of the anti-influenza virus monoclonal antibody.

8. A manufacturing method of the immunochromatographic test strip of claim 1, comprising the steps of:
   (1) applying a conjugate solution containing a conjugate in which an antibody or antigen immunologically reactive with an analyte is immobilized to a label in a line shape with a line width of 3-5 mm onto a portion of a pad-shaped porous material acting as a conjugate pad exclusive to the edge of the conjugate pad and drying the conjugate solution to form a conjugate section so as to create the conjugate pad having a portion other than the conjugate section as a sample-supplying section;
   (2) preparing an insoluble membrane support having at least one detecting section to which an antibody or antigen immunologically reactive with the analyte is immobilized; and
   (3) stacking the conjugate pad acquired at (1) on the upstream side of the insoluble membrane support prepared at (2) such that the lower surface of the sample-supplying section is not in contact with the insoluble membrane support while the lower surface of the conjugate section is in contact with the insoluble membrane support.

9. The immunochromatographic test strip according to claim 1, wherein a center line of the line-shaped conjugate section is disposed 10 to 20 mm downstream from the upstream end of the conjugate pad.

10. The immunochromatographic test strip according to claim 1, wherein the analyte is one or more selected from the group consisting of influenza A virus, influenza B virus, hepatitis B virus, hepatitis C virus, human immunodeficiency virus, human hemoglobin, hepatitis B antibody, hepatitis C antibody and human immunodeficiency virus antibody.

11. The immunochromatographic test strip according to claim 1, wherein the antibody is a monoclonal antibody.

12. The immunochromatographic test strip according to claim 1, wherein the antibody is a functional fragment of an antibody.

13. The immunochromatographic test strip according to claim 12, wherein the functional fragment of an antibody is a $F(ab')_2$ fragment.

14. The immunochromatographic test strip according to claim 12, wherein the functional fragment of an antibody is a Fab' fragment.

15. The immunochromatographic test strip according to claim 1, wherein the label is one or more selected from the group consisting of metal colloid particles, colored latex particles and magnetic particles.

16. The immunochromatographic test strip according to claim 15, wherein the metal colloid particles are one or more selected from the group consisting of colloidal gold particles and colloidal platinum particles.

17. The immunochromatographic test strip according to claim 1, wherein the conjugate pad comprises one or more selected from the group consisting of nonwoven fibers of paper, a cellulose mixture, nitrocellulose, polyester, acrylonitrile copolymer, glass and rayon.

18. The immunochromatographic test strip according to claim 1, wherein one or more control capture reagents are immobilized to the insoluble membrane support.

19. The immunochromatographic test strip according to claim 1, wherein the insoluble membrane comprises one or more selected from the group consisting of polyethylene, polyethylene terephthalate, nylons, glass, cellulose, cellulose derivatives and ceramics.

20. The immunochromatographic test strip according to claim 1, wherein the immunochromatographic test strip is fixed to a solid phase support and a film is laminated to the insoluble membrane support.

* * * * *